United States Patent [19]
McNeese

[11] Patent Number: 5,237,988
[45] Date of Patent: Aug. 24, 1993

[54] DEVICE FOR FASTENING AN ENDOTRACHEAL TUBE

[76] Inventor: Wesley G. McNeese, 126 N. Arbor Trails, Park Forest, Ill. 60466

[21] Appl. No.: 611,763

[22] Filed: Nov. 13, 1990

[51] Int. Cl.$^5$ ............................................. A61M 25/02
[52] U.S. Cl. ...................... 128/207.17; 128/DIG. 26; 24/306
[58] Field of Search ...................... 128/207.17, 207.14, 128/DIG. 15, DIG. 26; 604/174, 179, 180; 24/306, 442, 448, 3 B, 370, 16 R, 3 J, 3 C

[56] References Cited

U.S. PATENT DOCUMENTS

| | | | |
|---|---|---|---|
| 3,760,811 | 9/1973 | Andrew | 128/207.17 |
| 4,313,437 | 2/1982 | Martin | 128/207.17 |
| 4,520,813 | 6/1985 | Young | 128/207.17 |
| 4,774,944 | 10/1988 | Mischinski | 128/207.17 |

Primary Examiner—C. Fred Rosenbaum
Assistant Examiner—William Lewis
Attorney, Agent, or Firm—Jerome Goldberg

[57] ABSTRACT

A device for immovably securing an endotracheal tube after it had been inserted into the airway of the patient. A pair of supports are removably fastened to the air inlet end of the tube. A belt is secured to the supports and snugly positioned around the neck of the patient. Each end of the belt includes complementary coupling means for removably fastening on to one of the supports. An adhesive strip is positioned on the belt between the ends thereof for adhering to the back of the neck. The supports may include a pair of jaws acting as a spring for tightly embracing the tube.

15 Claims, 3 Drawing Sheets

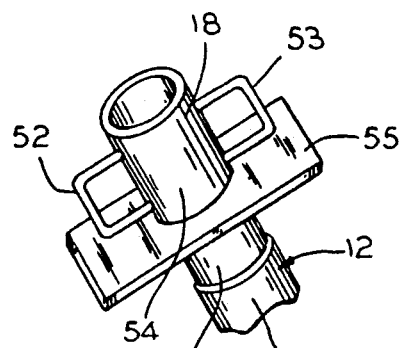
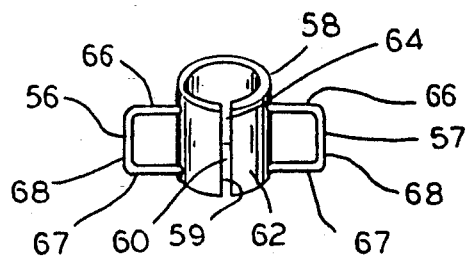
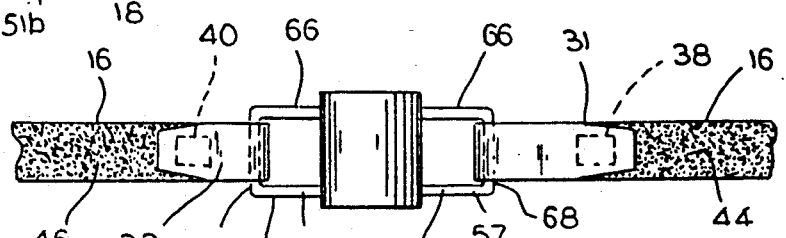
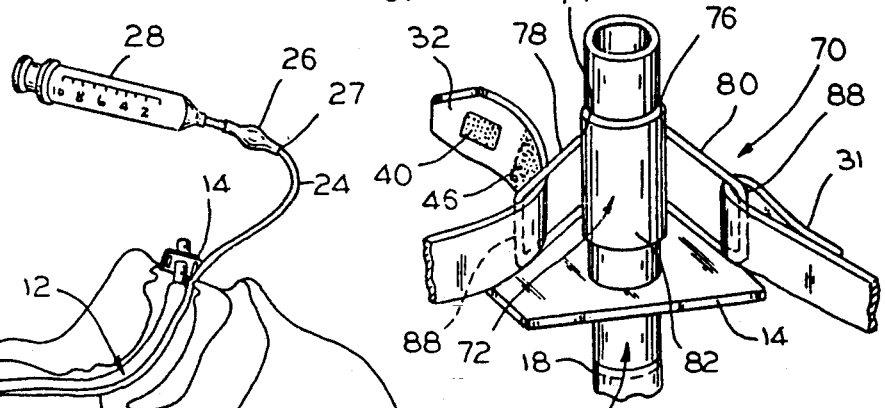
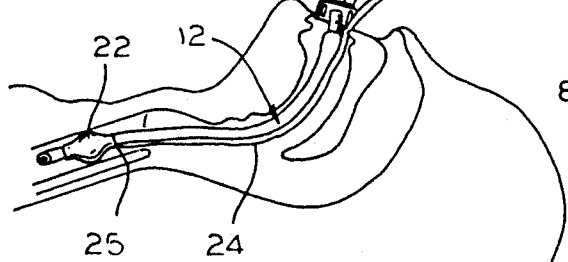
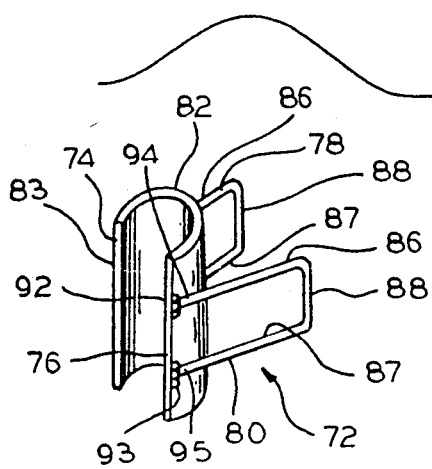
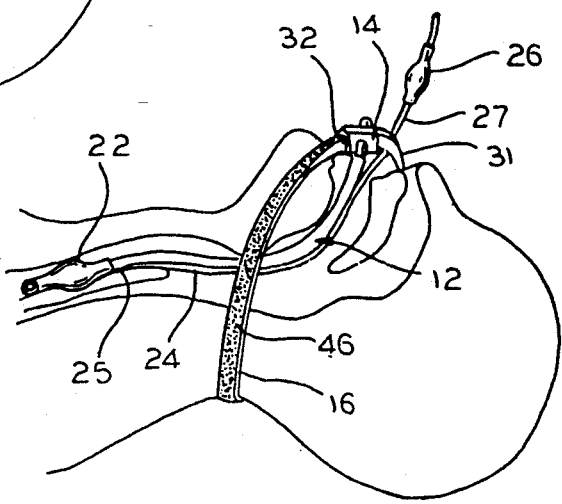

5,237,988

DEVICE FOR FASTENING AN ENDOTRACHEAL TUBE

BACKGROUND

This invention relates generally to a device for immovably securing a tube to a patient, and more specifically relates to a device for immovably securing an endotracheal tube to the patient.

When a patent's airway is partially or completely obstructed, the patient will exhibit respiratory distress. This could progress to respiratory arrest and even death. Therefore, it is imperative to keep the airways open. In the event of air blockage or when the patient has stopped breathing, an endotracheal tube is usually chosen initially as a means for quickly transmitting air directly to the lung area.

The endotracheal tube is inserted either into the nose or mouth, and then passed through the larynx and into the trachea. Generally, a cuff secured to the air outlet end of the tube is inflated and fills the space between the outside of the tube and the trachea when a sealed airway is required for mechanical ventilation.

Presently after the air outlet end of the endotracheal tube is positioned in the trachea, adhesive tape is usually used for securing the air inlet end of the tube to the face of the patient. Frequently, the tape would loosen due to head movement and the tube would migrate upward, sideways or drift downward and thereby appreciably reduce the effectiveness of the tube for providing needed air flow. Moreover, the tube could even descend into one of the bronchi and cause a lung to collapse. Thus, the medical attendant must be continually vigilent that the adhesive tape does not loosen, and that the endotracheal tube remains always immovably secured. This is often very difficult for the medical attendant to do, due to the many other duties and services he and she is required to perform, unless the patient has his or her private medical attendant or nurse.

The subject invention overcomes the aforedescribed problem and provides a device for immovably securing the endotracheal tube to the patient.

Therefore, a primary object of the invention is to insure efficient operation of an endotracheal tube and provide a continuous and proper air flow through the respiratory system of the patient.

Another primary object of the invention is to provide a fastening device for immovably securing an endotracheal tube to the patient.

Another object is to provide a fastening device for an endotracheal tube which is easily assembled and disassembled.

SUMMARY OF THE INVENTION

The present invention relates generally to an improved means for immovably securing a tube inserted inside the airway of a patient around the neck of the patient; and more specifically relates to a fastening device for immovably securing an endotracheal tube to the patient.

In accordance with one embodiment of the invention, a pair of supports are attached to the air inlet end of an endotracheal tube. Each support includes an opening. A belt having a pair of cooperating fasteners at each end thereof is positioned around the neck of the patient. One end of the belt is passed through one of the openings of the support and looped over the adjacent portion of the belt for the cooperating fasteners to fasten together; and similarly, the other end of the belt is passed through the opening of the other support and looped over the adjacent portion of the belt for the cooperating fasteners at the other end to fasten together, so that the endotracheal tube is in a secure and immovable position.

In accordance with another embodiment of the invention, the fastening device includes a clamp having a pair of jaws for removably attaching to the air inlet end of the endotracheal tube. A wing having an opening is attached to each jaw. A belt having cooperating fastening means at each end thereof is positioned around the neck of the patient. One end of the belt is passed through the opening of one of the wings and looped over to an adjacent portion of the belt for the cooperating fastening means at said one end to fasten together; and similarly, the other end of the belt is passed through the opening of the other wing for the cooperating fastening means at said other end to fasten together.

The cooperating fastening means comprises a fastening tab at the top side at each end of the belt. Inward from each fastening tab is a cooperating fastening section. The fastening tab may include a plurality of tiny hooks and the fastening section may include a plurality of tiny cooperating loops.

An adhesive strip is centrally located on the bottom side of the belt for adhering to the back of the neck of the patient, to further secure the endotracheal tube to the patient.

BRIEF DESCRIPTION OF THE DRAWINGS

Referring to the drawings in which the same characters of reference are employed to indicate corresponding similar parts throughout the several figures of the drawings.

FIG. 5 shows an alternate embodiment for the belt support of the fastening device;

FIG. 6 shows a modified embodiment for the belt support of FIG. 5;

FIG. 7 shows the belt attached to the belt support in FIG. 6;

FIG. 8 shows another alternate embodiment for the fastening device and illustrates a clamp arrangement removably attached to the endotracheal tube;

FIG. 9 is a perspective view illustrating the clamp used in FIG. 8;

FIG. 10 illustrates the endotracheal tube positioned in the airway of the patient;

FIG. 11 illustrates the fastening device of FIG. 1 securing endotracheal tube around the neck of the patient;

DESCRIPTION OF THE PREFERRED EMBODIMENT

Figure 1:
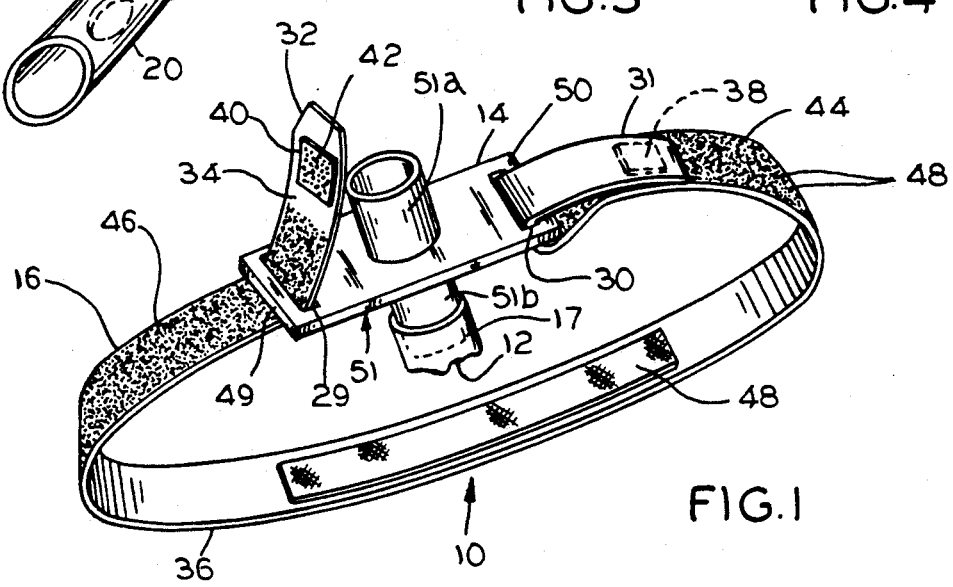
FIG. 1 is a perspective view of the device for fastening on to an endotracheal tube, embodying the principals of the invention.

Referring now more specifically to FIG. 1, the reference numeral 10 indicates generally a device for removably securing an endotracheal tube 12 to the neck of the patient. The securing device 10 comprises a support plate 14 and a belt 16.

Figure 2:
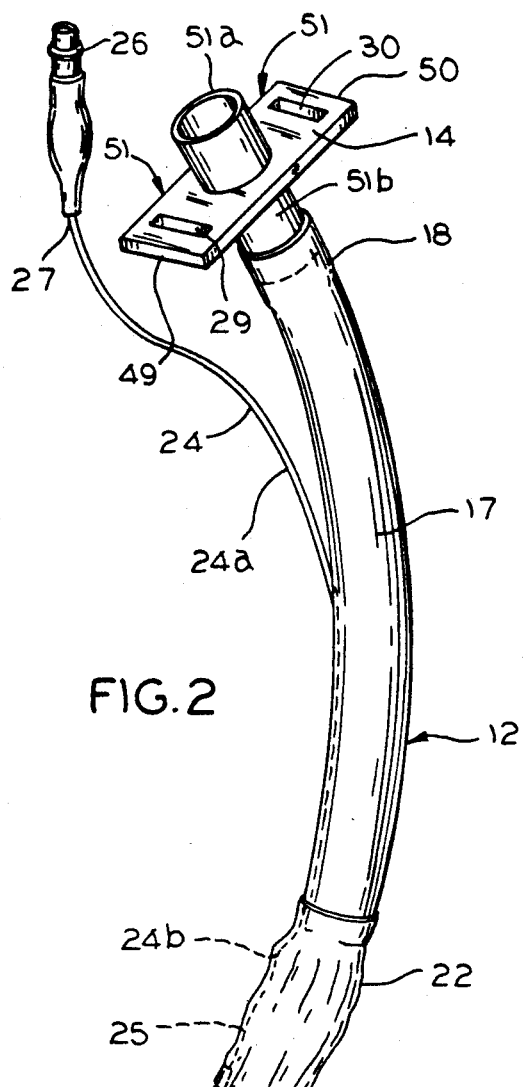
FIG. 2 is a perspective view of the endotracheal tube having an air expandable cuff.

As may be seen from FIG. 2, the endotracheal tube 12 is elongated, hollow and has a curved configuration. The tube 12 is operatively positioned in the trachea via the mouth and through the larynx. The tube 12 includes a body portion 17, an air inlet end 18 and an air outlet end 20. An inflatable cuff 22 is attached to the outside of the air outlet end 20.

A hollow air tubular member 24 is connected to the cuff 22 at the inner end 25 and to an air valve 26 at the outer end 27. The outer part 24a of the tubular member 24 is flexible and the remaining part 24b of the tubular member is secured to the side wall of the tube 12. A syringe 28 may be used to open the air valve 26 and inject air for passage through the tubular member 24 and into the cuff 22. The cuff should be inflated to a volume that provides adequate occlusion around the air outlet end 20 of the tube 14 without damaging adjacent areas of the trachea.

The support plate 14 has a substantially rectangular shape and includes a pair of spaced apart rectangular holes 29,30, each dimensioned to receive the width and thickness of the belt 16.

Figure 3:
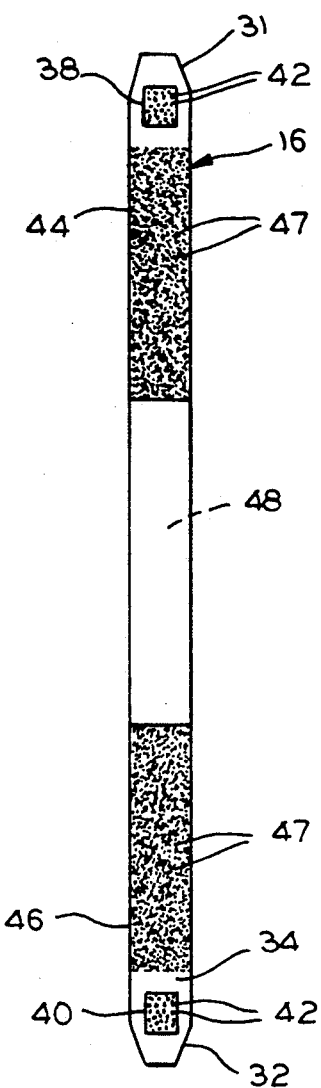
FIG. 3 is a top view of the belt for fastening around the neck of the patient.

The belt 16 is elongated and includes a pair of opposite ends 31,32, a top side 34 and a bottom side 36. A fastening tab 38 is attached to the top side 34 of the belt 16 at the end 31, and a similar fastening tab 40 is also attached to the top side 34 of the belt 16 at the end 32 (FIG. 3). Each fastening tab 38,40 includes a plurality of tiny hooks 42.

Inward from end 31 of the belt 16 and adjacent to the fastening tab 38 is a cooperating fastening section 44; and similarly, inward from belt end 32 and adjacent to fastening tab 40 is a cooperating fastening section 46. Each fastening section 44,46 is formed from a pile of material having a plurality of tiny loops 47.

The tiny hooks 42 of the fastening tabs 38,40 removably fasten respectively to the tiny loops 48 of the fastening sections 44,46. Hook fasteners and cooperating loop or pile fasteners sold under the trademark VELCRO are representative of the fasteners which may be used herein.

Figure 4:
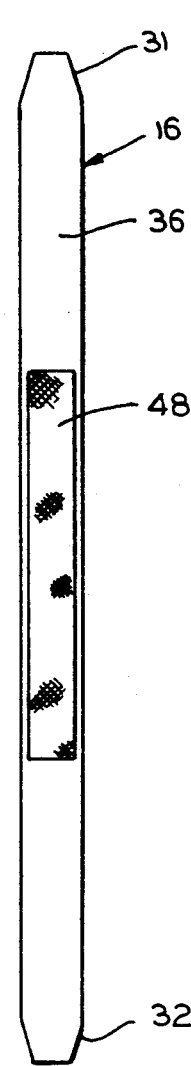
FIG. 4 is a bottom view of the belt.

The bottom side 36 of the belt 16 (FIG. 4) includes an adhesive strip 48, which is centrally positioned and spaced from the ends 31,32. The adhesive strip 48 may be covered with a protective outer paper covering (not shown).

To securely fasten the endotracheal tube 14 to the patient, the belt 16 is encircled around the patient's neck, and the belt end 31 is passed through hole 30 and the belt end 32 is passed through hole 29. The adhesive strip 48 on the bottom side of the belt 16 is centered at the back of the neck and any protective covering is removed, and the adhesive strip 48 is pressed against the back of the neck to adhere thereto.

The belt end 32 is tightened by looping the belt end 32 over the side 49 of the support plate 14 for attaching the fastening tab 40 to the fastening section 46. Similarly, the belt end 31 is tightened by looping the belt end 30 over the side 50 of the support plate 14 so that the fastening tab 38 attached to the fastening section 44.

After the belt ends 31,32 are secured and the adhesive strip 48 is adhering to the back of the neck, the endotracheal tube 12 is held in a secure and fixed position. Each belt end 31,32 may be readily adjusted if necessary, to vary the position of the tube 12.

As may be seen from FIG. 1, the plate 14 is part of an insert indicated generally by the reference numeral 51 and including an upper hollow annular portion 51a extending upward from the top side of plate 14 and a lower annular hollow portion 51b extending downward from the bottom side of plate 14. The lower annular portion 51b may be press fitted into or otherwise attached to the body 17 of the endotracheal tube 12. The hollow insides of the upper annular portion 51a and the lower annular portion 51b are in communication via an opening in the plate 14. The air inlet end 18 of the tube may include the insert 51.

In FIG. 5, another embodiment for supporting the belt 12 is shown. A pair of opposed and substantially "U" shaped brackets 52,53 are integrally formed to the outside of the upper annular portion 54 at the air inlet end 18 of the endotracheal tube 12. The brackets 52,53 provide supports for the belt ends 31,32. The blocking plate 55 prevents the annular portion from descending into the mouth of the patient.

As shown in FIG. 6, a pair of "U" shaped brackets 56,57 may be integrally formed spaced apart to the outside of a hollow sleeve 58. The sleeve 58 may be formed from a pliable and resilient material such as a suitable plastic.. The edges 59,60 of the side wall 62 of the sleeve 58 are shown spaced apart to provide an adjustible opening 64. The sleeve 58 press fits on to the outside of the tube air inlet end 18 of the tube 12. It may be positioned on the upper annular portion 51a or along the body 17 of the tube 12.

Each bracket 56,57 includes a pair of side bars 66,67 and a linking bar 68. The belt end 32 extends inside the bracket 56 and loops over the linking bar 68 of the bracket 56, so that the tab 40 fastens to the fastening section 46. Similarly, the belt end 31 extends inside the bracket 57 and loops over the linking bar 68 of the bracket 57 for the tab 38 to fasten to the fastening section 44.

Turning now to FIGS. 8 and 9, another embodiment of the invention of a device for securing an endotracheal tube 12 is shown and identified generally by the reference numeral 70. The securing device 70 includes a clamp 72 having a first jaw 74 and a second jaw 76 for clamping to the outside of the air inlet end 18 of the endotracheal tube 12. The clamp 72 includes a first wing 78 associated with the first jaw 74 and a second wing 80 associated with the second jaw 76. A web 82 connects the first jaw 74 with the second jaw 76.

The clamp 72 is a spring. In the normal position for the clamp 72, the first jaw 74 is spaced a minimum distance from the second jaw 76 or both jaws 74,76 may be in contact with each other. Upon pressing the wings 78,80 toward each other the first jaw 74 and second jaw 76 spread apart from their normal position for positioning on the outside of the air inlet end of the endotracheal tube 12. Upon releasing the pressing force from the wings 78,80, the jaws 74,76 embrace the tube 12 and resiliently lock thereon.

Each wing 78,80 has a substantially "U" shape and includes a pair of spaced apart side rods 86,87 and a linking rod 88 connecting the side rods 86,87. A pair of feet 92,93 are attached respectively to the inner ends 94,95 of the side rods 86,87 of wing 78, and a pair of feet 96,97 are attached respectively to the inner ends of the side rods 86,87 of the corresponding wings 78,80. A first pair of feet (not shown) are attached to the first jaw 74 and to the wing 78, and a second pair of feet 92,93 similar to the first pair of feet are attached to the second jaw 76 and wing 80.

When the linking rods 88 of wings 78,80 are pressed toward each other upon the application of an external force, the feet of the first jaw 74 and the feet 92,93 of the second jaw 76 cause the jaws 74,76 to move away from each other to provide a sufficiently large opening. The clamp 72 is then positioned around the endotrachael tube 12 and tightly embraced thereon when the external force is removed.

The belt end 32 extends inside the wing 78 and loops over the linking rod 88 of the wing 78, so that the tab 40 fastens to the fastening section 46. Similarly, the belt end 31 extends inside the wing 80 and loops over the linking rod 88 of the wing 80, for the tab 38 to fasten to the fastening section 44.

Figure 12:
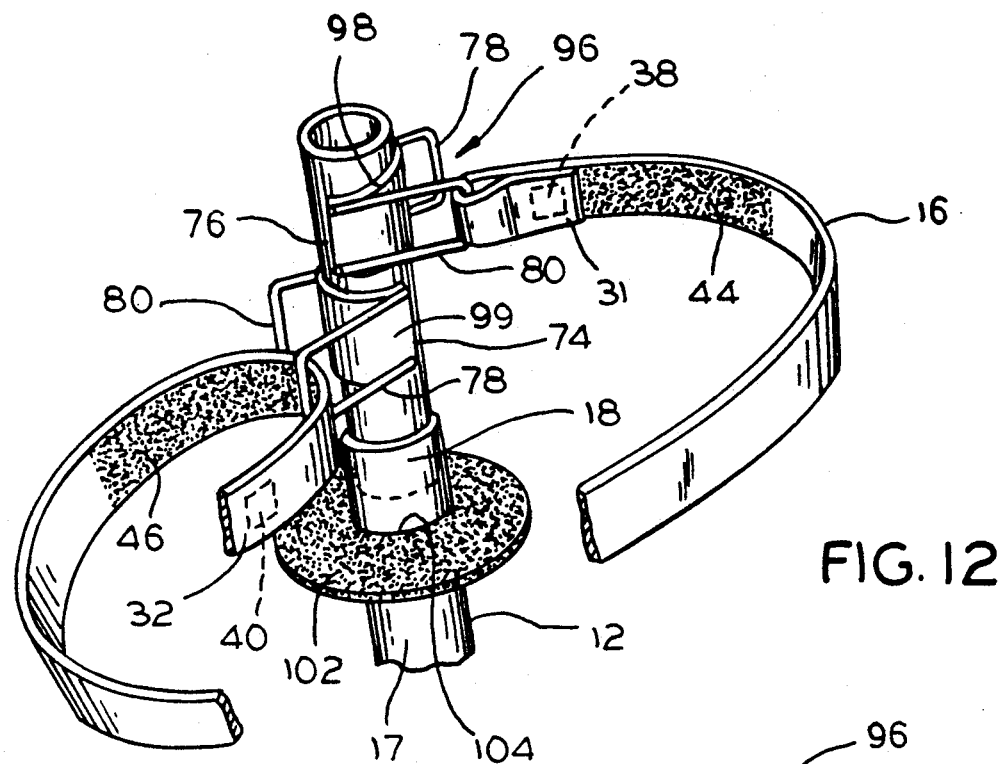
FIG. 12 illustrates still another alternative embodiment for the fastening device and shows in perspective a pair of clamps removably positioned on the air inlet end of the tube.
Figure 13:
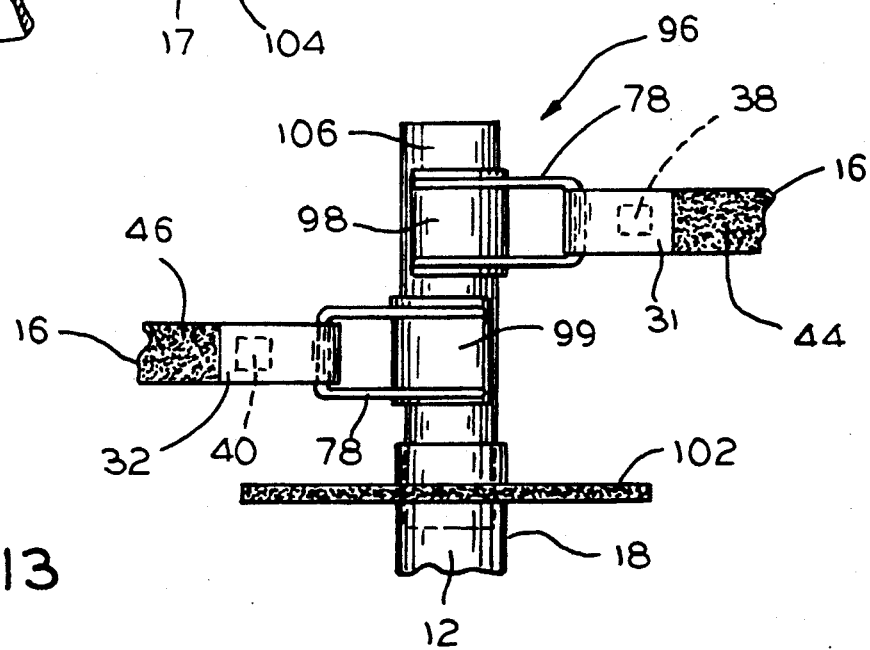
FIG. 13 is a side elevational fragmented view showing the belt fastened to the clamps embracing the air inlet end of the endotracheal tube.

Another embodiment for securing the endotracheal tube is shown in FIGS. 12 and 13 and identified generally by the reference numeral 96. A first clamp 98 is removably fastened to end 31 of the belt 16 and a second clamp 99 is removably fastened to end 32 of the belt 16. The first and second clamps 98,99 are similar to clamp 72 in FIG. 9, and each clamp 98,99 includes a first jaw 74, a second jaw 76, a first wing 78 associated with the first jaw 74 and a second wing 80 associated with the second jaw 76.

The clamps 98,99 are resiliently locked on the air inlet end 18 of the endotracheal tube 12 in the same manner as the clamp 72 is fastened on the tube 12. By having the two clamps 98,99 fastened on the tube 12, the position of the tube 12 may be more precisely adjusted. Also the tightness of the belt 16 around the patient is more easily controlled.

An annular washer 102 having an opening 104 is inserted on the air inlet end 18 of the tube 12 to provide a cushion buffer between the lips of the patient and the fastening device 96. The washer 102 is formed from a felt or other suitable soft and non-abrasive material which will not cause sores on the lips from contact therewith.

Although the fastening device 10, the fastening device 70 and the fastening device 96 refer to the immovable fastening of an endotracheal tube to the patient, it should be understood and evident from the description that the fastening devices 10,70 and 96 would also be suitable for immovably securing other type tubes or devices to the patient.

Various modifications of the invention of a fastening device for an endotracheal tube described herein and for other type tubes and apparatuses, are within the spirit, contemplation and scope of the invention, the scope of which is limited solely and defined by the appended claims.

I claim:

1. A fastening device for securing a hollow tube after the tube is inserted into the airway of the patient, said tube having an air inlet end for positioning on the outside of the patient and an air outlet end, and said device comprising:
    support means attached to the air inlet end of the tube;
    a belt positioned around the neck of the patient, said belt including a top side, a bottom side and opposite ends;
    at least one end of the belt having complementary fastening means for removably securing the belt on said support means; and
    an adhesive strip interposed on said belt between the ends thereof for adhering to the neck of the patient.

2. The fastening device of claim 1, wherein said fastening means comprises:
    a first fastening member positioned at one end of said belt; and
    a second fastening member positioned adjacent said first fastening member, said one belt end being supported on said support means to overlap the adjacent portion to the belt so that the first fastening means removably fastens to said second fastening means.

3. The fastening device of claim 2 further includes:
    a third fastening member positioned at the other end of said belt; and
    a fourth fastening member positioned adjacent said third fastening member, said other belt end being supported on said support means to overlap the adjacent portion of the belt so that the third fastening means removably fastens to said fourth fastening means.

4. The fastening device of claim 2, wherein one of said fastening means includes a plurality of loops and other of said fastening means includes a plurality of hooks for fastening to said loops.

5. The fastening device of claim 1, wherein said support means includes a clamp for removably positioning on said air inlet end of said tube, said clamp having an opening formed therein, said one end of the belt passing through said opening and overlapping the adjacent portion of the belt, so that said complementary fastening means secure together.

6. The fastening device of claim 5, wherein said clamp includes:
    a first jaw and a second jaw having a normal position; and a first wing having said opening and attached to the first jaw and a second wing attached to said second jaw, said one end of the belt being supported on said first wing, said wings being pressed toward each other for spreading apart said jaws from their normal position when positioned on the air inlet end of said tube.

7. The fastening device of claim 6, wherein each of said wings have a substantially "U" shaped configuration including:
    a pair of spaced apart side rods having inner ends attached to one of said jaws;
    a linking rod connecting the outer ends of the rod together; and
    said one end of the belt passing through the space between said side rods and being supported on said linking rod when overlapping the adjacent portion of the belt, so that said complementary fastening means secure together.

8. A fastening device for securing a hollow tube after the tube is inserted into the airway of the patient, said tube having an air inlet end for positioning on the outside of the patient and an air outlet end, and said device comprising:
    support means attached to the air inlet end of the tube;
    a belt positioned around the neck of the patient, said belt including a top side, a bottom side and opposite ends;

an adhesive strip interposed on said belt between the ends thereof for adhering to the neck of the patient;

a first fastening member positioned at one end of said belt; and a second fastening member positioned at a portion of the belt adjacent said first fastening member, said one belt end being supported on said support means to overlap the adjacent portion of the belt so that the first fastening means removably fastens to said second fastening means for securing the belt on the support means.

9. The fastening device of claim 8, wherein said first and second fastening members are positioned on said top side of said belt and said adhesive strip is positioned on the bottom side of said belt.

10. A fastening device for securing an endotracheal tube after the tube has been inserted into the airway of the patient, said tube having an air inlet end and an air outlet end, and said device comprising:

a spring clamp having support means, said clamp including a first jaw and a second jaw, said jaws having a normal position, said jaws resiliently urging toward each other when spread apart from said normal position for positioning on the outside of the air inlet end of the tube;

a belt means for positioning around the neck of the patient; and said belt means including complementary fastening means located at one end of the belt for removably attaching said belt means to said support means.

11. The fastening device of claim 10, wherein said support means includes a pair of substantially "U" shaped brackets, each of said brackets including spaced apart side bars and a linking bar attaching the side bars together, said one end of the belt being supported on the linking bar of one of said brackets and the other end of the belt being supported on the linking bar of the other bracket.

12. The fastening device of claim 10, wherein said belt means includes a top side, a bottom side and a pair of opposite ends, and said device further comprises:

a first wing including an opening attached to said first jaw;

a second wing including an opening attached to said second jaw; and said complementary fastening means including:

a first fastening member positioned at one of said belt ends; and a second fastening member positioned at a portion of the belt adjacent said said first fastening member, said one belt end passing through the opening of said first wing to overlap the adjacent portion of the belt so that the first fastening member removably fastens to said second fastening member, said other end of the belt being associated with said second wing.

13. The fastening device of claim 12 further includes;

a third fastening member attached to the other end of said belt ends; and a fourth fastening member positioned adjacent said third fastening member, said other belt end passing through the opening of said second wing to overlap the adjacent portion of the belt so that the third fastening member removably fastens to said fourth fastening member.

14. The fastening device of claim 12 wherein said first and second fastening means are attached at the top side of the belt, and said device further includes:

an adhesive strip positioned between said ends of the belt and attached to the bottom side of the belt.

15. The fastening device of claim 14 further includes:

a second spring clamp having a second support means, said second clamp including a third jaw and a fourth jaw, said third and fourth jaws having a normal position and said jaws resiliently urging toward each other when further spread apart from said normal position for positioning on the outside of said air inlet end of the tube; and a second complementary fastening means located at the other end of the belt for fastening said other belt end to said second support means.

* * * * *